United States Patent [19]
Bergkuist et al.

[11] Patent Number: 6,123,820
[45] Date of Patent: Sep. 26, 2000

[54] SENSOR CARTRIDGES

[75] Inventors: Carolyn Bergkuist, Lexington, Mass.; Richard P. Buck; Vasile V. Cosofret, both of Chapel Hill, N.C.; Chung-Chuin Liu, Cleveland, Ohio; Richard A. Lucic, Durham, N.C.; John P. Moriarty, Lexington, Mass.; Michael R. Neuman, Cleveland, Ohio; Richard M. Bucchianeri, Westford, Mass.

[73] Assignees: Grupo Ch-Werfen, S.A., Spain; Duke University, Durham; The University of North Carolina, Cpahel Hill, both of N.C.; Case Western Reserve University, Cleveland, Ohio

[21] Appl. No.: 09/090,992

[22] Filed: Jun. 5, 1998

[51] Int. Cl.[7] .................................................. G01N 27/26
[52] U.S. Cl. ........................................ 204/411; 204/409
[58] Field of Search ................................... 204/409, 411, 204/412; 422/82.01

[56] References Cited

U.S. PATENT DOCUMENTS

| | | | |
|---|---|---|---|
| 3,658,478 | 4/1972 | Spergel et al. | 23/253 R |
| 4,361,539 | 11/1982 | Weinberg et al. | 422/68 |
| 4,361,540 | 11/1982 | Weinberg et al. | 422/68 |
| 4,443,407 | 4/1984 | Weinberg et al. | 422/68 |
| 4,734,184 | 3/1988 | Burleigh et al. | 204/409 |
| 4,818,361 | 4/1989 | Burgess et al. | 204/406 |
| 4,871,439 | 10/1989 | Enzer et al. | 204/401 |
| 4,889,611 | 12/1989 | Blough, Jr. | 204/411 |
| 5,200,051 | 4/1993 | Cozzette et al. | 204/403 |
| 5,338,435 | 8/1994 | Betts et al. | 204/406 |
| 5,387,329 | 2/1995 | Foos et al. | 204/415 |
| 5,571,396 | 11/1996 | Cormier et al. | 422/82.03 |
| 5,700,360 | 12/1997 | Chan et al. | 204/400 |

FOREIGN PATENT DOCUMENTS 0 772 043 A2  5/1997  European Pat. Off. .

OTHER PUBLICATIONS

Davies et al, "The Potential of Hydrogen (sic, Hydrogel) Polymers in Sensor Applications", *Selective Electrode Rev.*, 1991, vol. 13, pp. 159–226.

Primary Examiner—T. Tung
Assistant Examiner—Alex Noguerola
Attorney, Agent, or Firm—Nixon & Vanderhye P.C.

[57] ABSTRACT

Sensor cartridges include a fluid constituent-selective sensor membrane in direct sealing contact with a face of a flow-through sample cell in surrounding relationship to a sensor port. The sensor membrane has sufficiently large surface area so as to entirely cover the sensor port and establish an annular region in surrounding relationship thereto. It is this annular region which is in direct contact with a corresponding region of the sample cell face so as to provide self-sealing capabilities. The sensor cartridge most preferably includes a flow-through sample cell having a zig-zag or serpentine flow channel so as to provide a series of sensor ports on both of the opposed cell faces. The faces of the sample cell are most preferably provided with recessed regions which define a series of land surfaces each of which surrounds a respective one of the sensor ports. A pair of sensor arrays having a corresponding series of sensors are thus juxtaposed with a respective land surface of the sample cell face so as to sandwich the sample cell therebetween. A two-part "clamshell" housing houses the sensor arrays and the sample cell sandwiched therebetween.

38 Claims, 7 Drawing Sheets

SENSOR CARTRIDGES

FIELD OF INVENTION

The present invention relates generally to the field of sensors used in the analysis of fluid properties. In preferred forms, the present invention is embodied in a sensor cartridge which is especially adapted for use in biomedical applications so as to assist in the analysis of multiple physical parameters and/or chemical constituents of small volume samples of bodily fluids (e.g., whole blood).

BACKGROUND AND SUMMARY OF THE INVENTION

It is oftentimes desirable in biomedical applications to analyze multiple physical properties and/or constituents of small volume samples of a patient's bodily fluid. For example, samples of a patient's whole blood are oftentimes analyzed and/or monitored so as to provide information regarding blood analytes such as pH, $PCO_2$, $PO_2$, $K^+$, $Na^+$, $Ca^{2+}$, $Cl^-$, and the like. Information derived from blood analytes in a sample is compared to normal physiological functions and homeostasis profiles and thereby used by the attending physician for diagnostic purposes and/or to control life support systems.

Systems which employ electrochemical electrodes for detecting constituents of a bodily fluid, for example whole blood, are in and of themselves well known as evidenced from U.S. Pat. Nos. 3,658,478 to Spergel et al, 5,387,329 to Foos et al, 5,338,435 to Betts et al, 4,734,184 to Burleigh et al, 4,361,539 to Weinberg et al and 5,200,051 to Cozzette et al (the entire content of each patent being expressly incorporated hereinto by reference). While the sensor systems disclosed in the prior art may reasonably be satisfactory for their intended purposes, further improvements to decrease cost and to increase manufacturing yield, reliability, shelf life, operating life and user convenience are still desired. In order to realize all these further improvements simultaneously, there have been a number of recent efforts and subsequent patents to miniaturize the sensors themselves and to fabricate them by techniques recently made available by developments in integrated circuit technology. In this regard, integrated circuit technology allows sensors to be fabricated in a planar format whereby thin layers of materials are applied successively to a base dielectric substrate using thick-film and/or thin-film techniques. The manufacture of planar sensors can be significantly automated to allow production in quantity and at lower cost. Planar sensors can be made smaller and configured more closely together, reducing the sample volume requirements.

Historically, the design of microsensors has largely involved simply the miniaturization of macrosensor technology. Performance expectations, however, have not been realized—in large measure because of the poor chemical stability of small sensor assemblies as evidenced both by short operating life and by unacceptable drift rates over that life. Additional constraints are placed on the design of microsensor that are to be manufactured in compact arrays. To the performance criteria currently applied in the evaluation of conventional sensing electrodes must be added an important further constraint—namely, in order to exploit these developments in integrated circuit technology and realize the economies of bulk manufacture in compact arrays, it is necessary that all sensor types have generally the same design and structure involving more or less the same fabrication techniques.

For example, most prior art systems include a sensor array which itself defines one wall of the flow channel. Thus, in order to limit sample volume requirements, the channel cross-section and/or length must be reduced which, in turn, limit the sensor membrane cross-section and its total volume. The adverse consequence of limiting membrane cross-section and/or volume under these circumstances is that the useful life of the sensor is reduced.

On the other hand, if, in order to increase the membrane diameter, the width of the channel is increased locally without increasing the cross-section of the channel throughout, then one or more fluid pockets will be formed in the flow channel which tends to aggravate any clean-out problems and increases the sample volume needed to assure a clean, uncontaminated sample segment in front of the sensors during the actual time of measurement. Local increases in the cross-section of the channel also disadvantageously promote sample degassing.

The limits to the cross-sectional area of the membrane also limits the bonding area between the membrane and its support substrate and any possible sealing area between the membrane and the flow channel. The limited bonding area between the membrane and the substrate requires very tight tolerances for membrane deposition and a relatively frequent incidence of loss of adhesion. Sensor failures can thus ensue as a direct consequence of such limited bonding areas.

In many prior art sensor systems, the entire surface area of the membrane is exposed to the sample stream. For example, as disclosed in the above-cited Betts et al '435 and Burleigh et al '184 patents, the membrane is thereby entirely exposed to the sample in the flow path. However, the fact that the entire surface area of the membrane is exposed to the sample stream leaves no opportunity for mechanical capture of the membrane between the substrate layer supporting the membrane and the layer defining the flow channel of the sensor module. Furthermore, in those prior art systems where the entire membrane area is exposed to the sample stream, bonding between the membrane and the substrate is achieved solely by direct adhesion, and so membranes that do not chemically bond to the substrate surface may delaminate, thereby again causing sensor failures.

The problems discussed above become particularly acute when multiple sensor arrays are provided in clusters so as to be capable of detecting a corresponding multitude of physical properties and/or constituents in a single fluid sample.

What has been needed in this art, therefore, is a sensor cartridge having plural (i.e., at least two, or more) fluid constituent-selective membranes which are self-aligning and self-sealing with respect to a fluid sensing port associated with the sensor cartridge's fluid flow path. It is toward fulfilling such a need that the present invention is directed.

Broadly, the present invention is embodied in a sensor cartridge in which a fluid constituent-selective sensor membrane is in direct sealing contact with a face of a flow-through sample cell entirely around a sensor port of the flow channel. In other words, the sensor membrane has sufficiently large surface area so as to entirely cover the sensor port and also establish an annular region in surrounding relationship to the sensor port. It is this annular region which is in direct contact with a corresponding region of the sample cell face so as to provide self-sealing capabilities. Moreover, the sensor membrane is self-aligning with the sensor port since it has a sufficiently large area to ensure complete coverage of the sensor port. Thus, according to the present invention the diameter of the sensor membrane is no longer dependent on the cross-sectional dimension of the flow channel supplying sample fluid to the sensor port.

In a particularly preferred embodiment of this invention, the sensor cartridge includes a flow-through sample cell having a zig-zag flow channel so as to provide a series of sensor ports on both of the opposed cell faces. A pair of sensor arrays having a corresponding series of individual sensors are thus juxtaposed with a respective sample cell face so as to sandwich the sample cell therebetween. The individual sensors are provided with sensor membranes selective to a desired fluid constituent to be determined and are connected electrically to peripheral detection hardware. Each of the individual sensors thus electrochemically determines a particular fluid constituent which is communicated electrically to the peripheral hardware where it may be displayed in human-readable form.

Furthermore, according to the present invention, the ratio of the membrane surface area exposed to the sample stream compared to the total membrane surface area is such that most of the membrane surface is not subject to extraction into the sample stream. Thus, the bulk of the membrane functions as a reservoir of critical components against the early depletion of the membrane.

The sandwiched sample cell and sensor arrays are most preferably contained within a two-part "clamshell" housing. The term "clamshell" as used herein and in the accompanying claims is meant to refer to a two part, bilaterally symmetrical outer shell that encases the flow chamber on at least two of its sides. The housing may or may not include hinge structures so as to allow the two parts thereof to be hingedly moved relative to one another and thereby gain access to the flow chamber. The housing includes biasing members (most preferably in the form of a resilient elastomeric pad) which serve to bias the sensor membranes into direct sealing contact with their respective sample cell faces around the sensor port.

The arrangement of the present invention therefore offers an important advantage in terms of the angle of approach of the sample path to the sensor membranes in that the sample stream contacts the membrane only at its center. As a result, single, discrete sensors on separate individual chips may be aligned contiguously without unacceptably increasing the potential for leaks in the fluid path. This, in turn, leads to significant manufacturing and test advantages.

Further aspects and advantages of this invention will become more clear after careful consideration is given to the following detailed description of the preferred exemplary embodiment thereof.

BRIEF DESCRIPTION OF THE DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
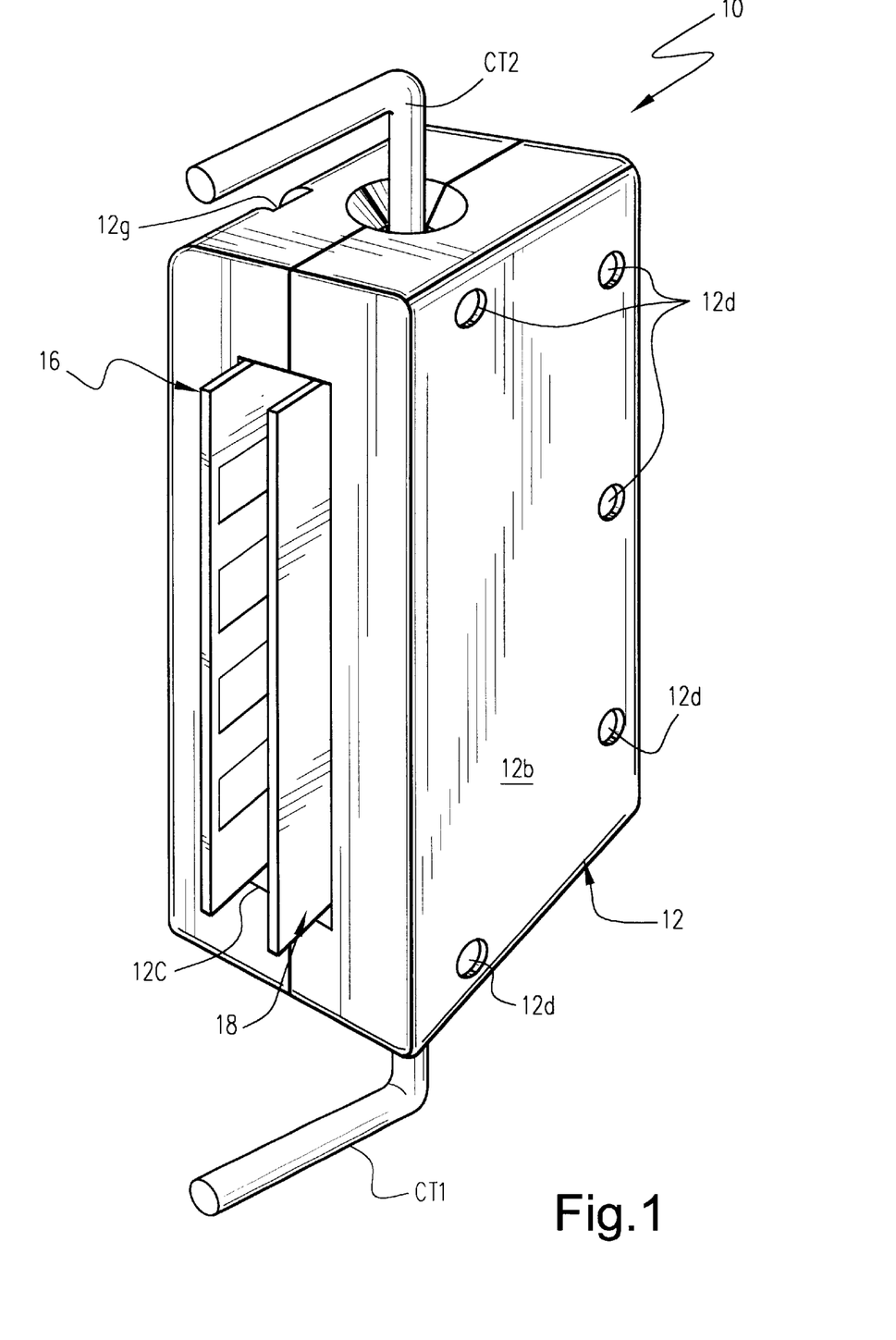
FIG. 1 is an external perspective view of one embodiment of the sensor cartridge according to this invention.
Figure 2:
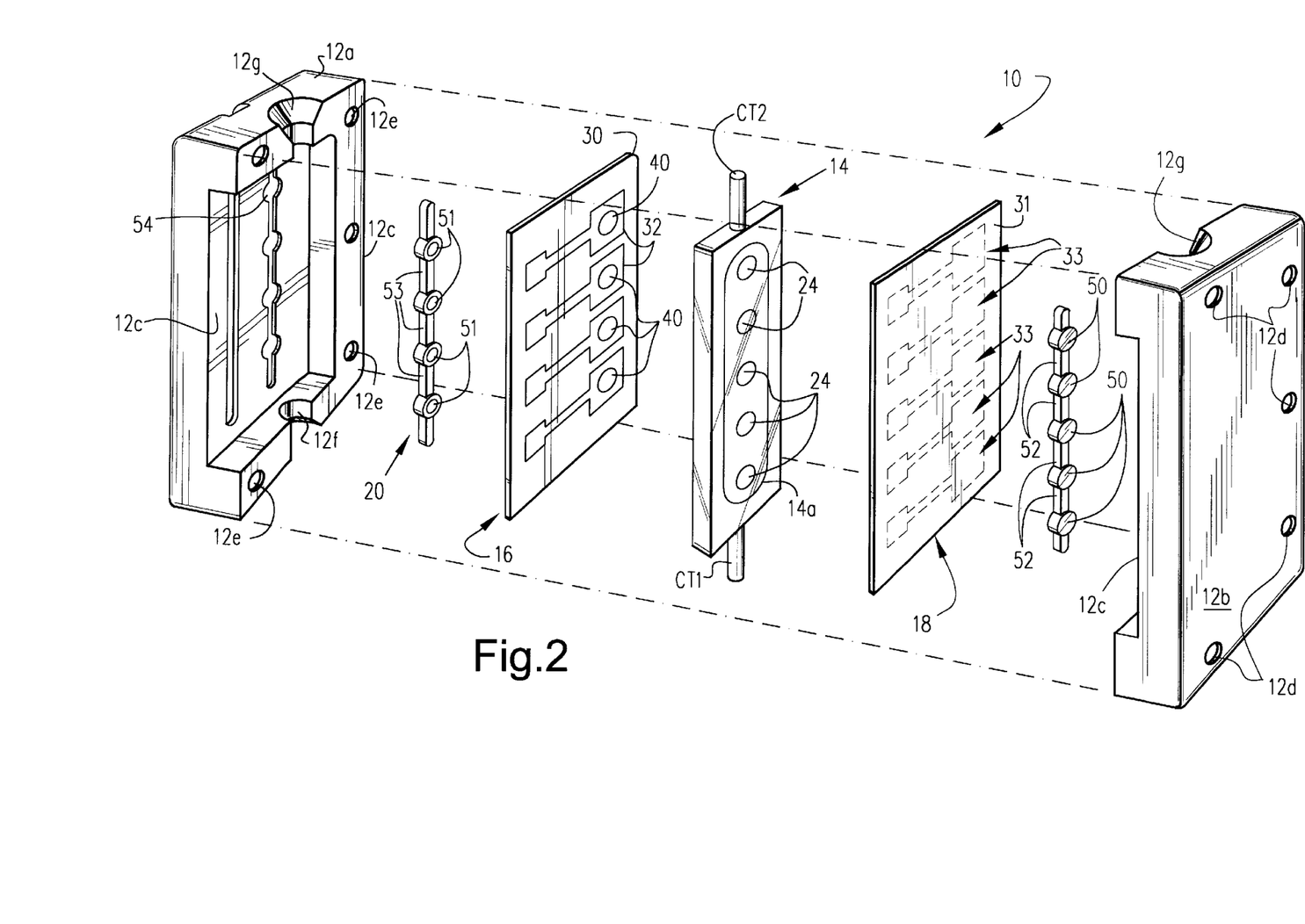
FIG. 2 is an exploded perspective view of the sensor cartridge depicted in FIG. 1.
Figure 3:
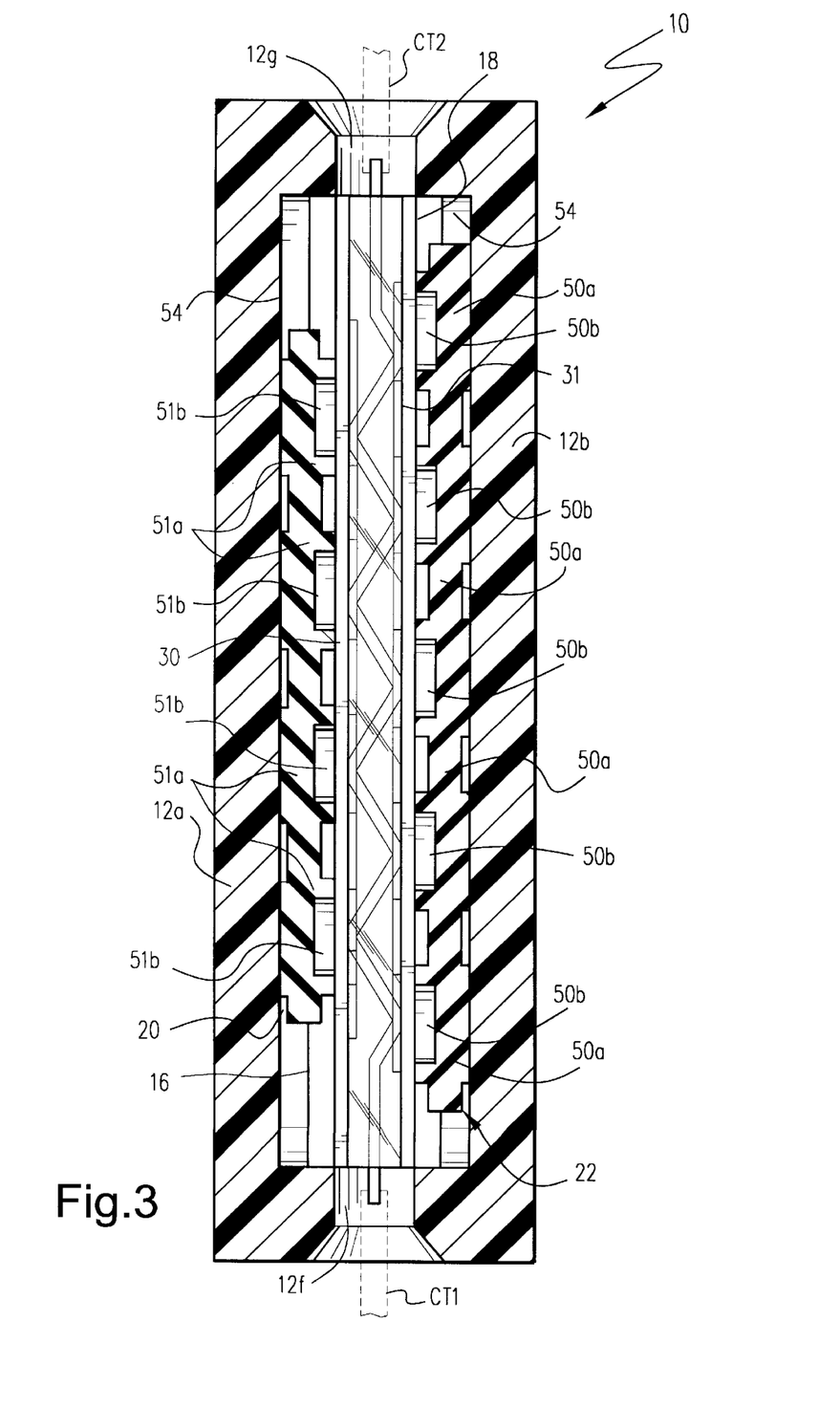
FIG. 3 is a longitudinal cross-sectional view of the sensor cartridge depicted in FIG. 1.

An embodiment of the sensor cartridge 10 according to the present invention is depicted in accompanying FIGS. 1–3. As shown therein, the sensor cartridge 10 includes a housing 12 formed of a pair of mateable external housing components 12a, 12b. The housing 12 houses a flow-through sample cell 14 preferably formed from a rigid transparent or translucent thermoplastics material (e.g., an acrylic polymer). The sample cell 14 is sandwiched between a pair of sensor arrays 16, 18 each of which is forcibly pressed against a respective opposed face 14a, 14b of the sample cell 14 by a respective biasing member 20, 22. The mateable housing components 12a, 12b define a longitudinally extending edge slot 12c to permit simple and convenient contact with an electrical connector (not shown) provided with the host analyzer. In such a manner, electrical signals generated or modified at individual ones of the sensors 16a, 18a associated with the sensor arrays 16, 18, respectively, which are conducted by other electrical components of the cartridge (e.g., via leads, tracks, contact pads, and the like) can be connected and faithfully conveyed to the host analyzer for further processing.

The housing components 12a, 12b are fixed to one another by any convenient mechanical means. In the depicted embodiment of the sensor cartridge 10, such means just happen to be screws (not shown) which are threadably engaged within the screw holes 12d, 12e of housing components 12b, 12a respectively. The housing components 12a, 12b could, however, be provided with integral mechanical latch assemblies (e.g., male/female latches) and/or hook and loop latches (e.g., Velcro-brand fasteners) if desired.

Figure 4:
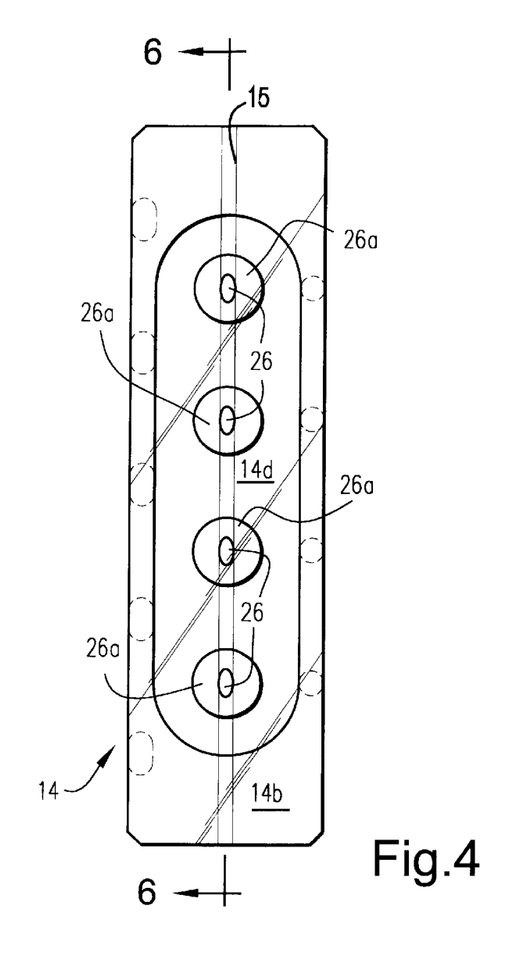
FIG. 4 is a planar view of one of the opposed faces of the sample cell employed in the sensor cartridge of this invention.
Figure 5:
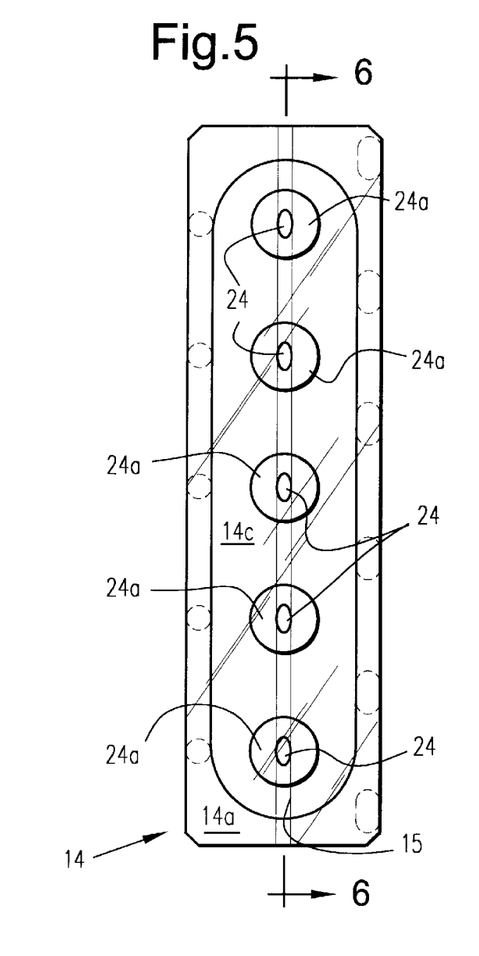
FIG. 5 is a planar view of the other of the opposed faces of the sample cell employed in the sensor cartridge of this invention.
Figure 6:
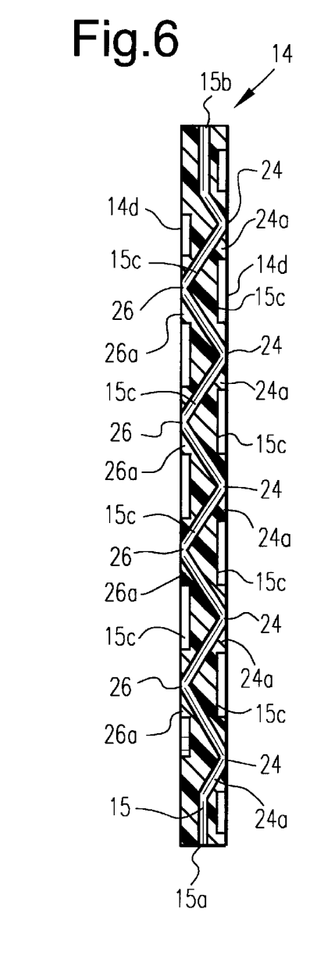
FIG. 6 is a cross-sectional view of the sample cell employed in the sensor cartridge of this invention as taken along lines 6—6 in each of FIGS. 4 and 5.

As is perhaps best shown in FIGS. 4–6, the sample cell 14 includes a zig-zag (serpentine) flow channel 15 formed by well known machining and/or molding techniques and a series of sensor ports 24, 26. The flow channel 15 is most preferably of capillary size—that is, less than about 1 mm in diameter. Each of the sensor ports 24, 26 is in fluid communication with the channel 15 and is exposed on a respective face 14a, 14b of the sample cell 14. Each of the faces 14a, 14b of the sample cell 14 includes respective recessed regions 14c, 14d which establish raised circular land regions 24a, 26a. These land regions 24a, 26a are centrally occupied by a respective one of the sensor ports 24, 26. Each of the land regions 24a, 26a thereby surround a respective one of the surface-exposed sensor ports 24, 26. Moreover, the upper surfaces of the land regions 24a, 26a are raised relative to the recessed regions 14c, 14d and thus do not extend outwardly from the faces 14a, 14b of the sample cell 14. Instead, the upper surfaces of the land regions 24a, 26a are coplanar with their respective faces 14a, 14b.

The flow channel 15 includes a fluid inlet 15a and a fluid outlet 15b which may be fluid-connected to inlet and outlet capillary tubing CT1 and CT2, respectively (see FIGS. 1 and 2), to allow a fluid sample (e.g., whole blood) to flow through the sample cell 14. Capillary tubing CT1 and CT2 are each most preferably rigid stainless steel capillaries and exit the housing 12 via end apertures 12f, 12g. In this regard, the capillary tubing may conveniently be provided with a substantially right angle bend so as to allow fluid connections for the sample stream to enter and exit the housing from the same face as the electrical connections.

The sensor ports 24, 26 are serially fluid connected by flow channel segments 15c so that the overall flow channel 15 has a general zig-zag or serpentine path. In this regard, the flow channel segments 15c form an angle (e.g., between about 15° to about 80°, preferably about 30°) relative to the plane of sample cell faces 14a, 14b. In such a manner, therefore, the channel segments 15c will fluid-connect the sensor ports 24, 26 alternately across the thickness of the sample cell 14.

Figure 7:
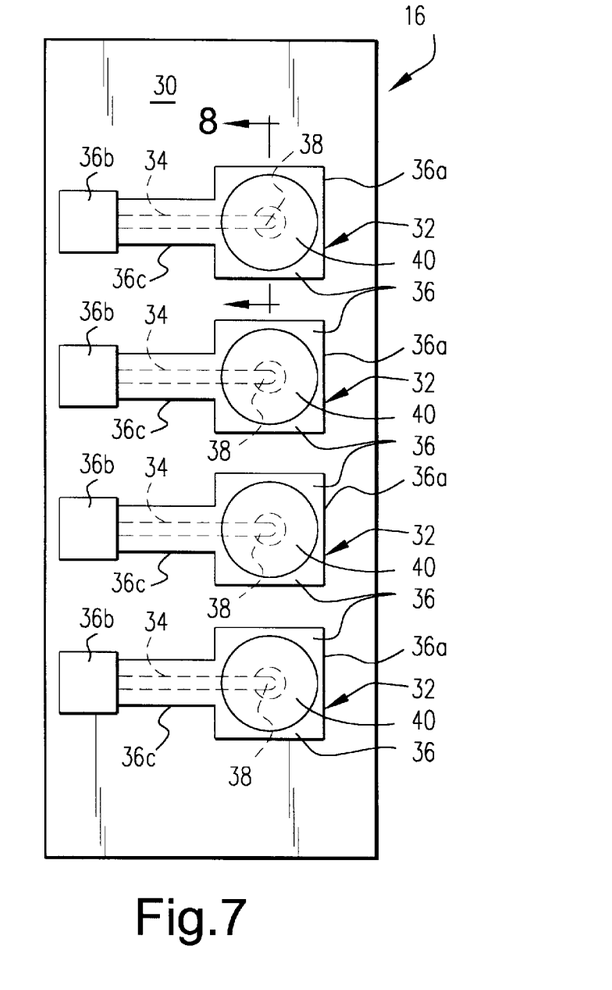
FIG. 7 is a planar view of a representative sensor array employed in the sensor cartridge according to this invention.
Figure 8:
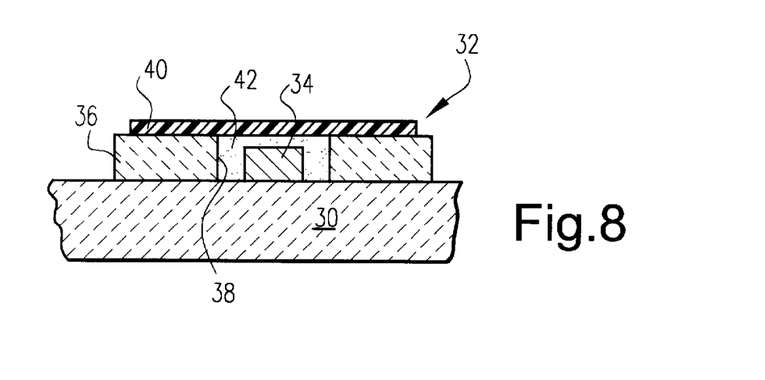
FIG. 8 is a cross-sectional view through a representative sensor associated with the sensor array depicted in FIG. 7 as taken along lines 8—8 therein.

As noted above, the sample cell 14 is sandwiched between a pair of sensor arrays 16, 18 within the interior of the housing 12. Accompanying FIGS. 7 and 8 depict in greater detail the sensor array 16. Sensor array 16 is, however, representative of sensor array 18 except that the latter is provided with one additional sensor corresponding in number to the sensor ports 26 provided on the sample cell face 14b. Thus, the discussion which follows with respect to sensor array 16 is equally applicable structurally and functionally to the sensor array 18 and wherever possible, structures of sensor array 18 which are visible in the accompanying drawing FIGURES corresponding to structures of sensor array 16 are noted below parenthetically.

As can be seen in FIGS. 7 and 8, the sensor array 16 (18) is, in one configuration, composed of a ceramic support substrate 30 (31) carrying a number of electrochemical sensors 32 (33) situated side-by-side along the lengthwise dimension of the support substrate 30 (31). Each of the sensors 32 (33) includes an electrical conducting layer 34 covered by a ceramic glaze layer 36. The electrical conductive layer 34 is disposed on the electrically insulating substrate 30 so as to make electrical connection between an internal sensing electrode 34a and an electrical connection pad 34b. The internal sensing electrode 34a may be an exposed portion of the metal layer forming the electrical conductive layer 34 or it may be covered with a thin layer of another material 34c, such as silver chloride, that has chemical and electrical properties necessary for the desired measurement.

The ceramic glaze layer 36 is formed in such a manner as to include a generally rectangular sensing region 36a and an intermediate region 36c that covers the electrical conductive layer 34 between the internal sensing electrode 34a and the electrical connection pad 34b. The electrical contact pad 34b allows convenient and simultaneous electrical connection of all the individual sensors to the host analyzer whereby electrical signals generated or modified at individual ones of the sensors 16a, 18a associated with the sensor arrays 16, 18, respectively can be connected and faithfully conveyed to the host analyzer for further processing.

The ceramic glaze layer 36 defines a generally circularly shaped sensor well 38 superposed over the terminal end of the electrical conductive layer 34 containing the internal sensing electrode 34a. The depth of the well is determined by the thickness dimension of the ceramic glaze layer 36 which, in turn, is selected according to the particular physical parameter and/or constituent of the fluid to be detected. Generally, however, thicknesses of between about 5 $\mu$m to about 140 $\mu$m will suffice for the ceramic glaze layer 36 when the sensors 32 are employed to detect the physical parameters and/or constituents of whole blood. In addition to defining the sensor well 38, the ceramic glaze layer 36 serves to isolate adjacent ones of the sensors 32 (and their associated leads, tracks, and contact pads) chemically and electrically from one another.

The sensor wells 38 are individually covered entirely by sensor membranes 40 cast from a conventional solution of polymeric permselective material. The membranes 40 are of sufficient size as to establish an annular peripheral region which entirely bounds the sensor ports 24, 26 when the sensor arrays 16, 18 are placed in contact with the surfaces of their respective sample cell faces 14a, 14b. It is this bounded annular peripheral region of the membranes 40 which is brought into direct sealing contact with a respective surface of land regions 24a, 26a when the sensor cartridge 10 is fully assembled thereby preventing fluid leakage.

Preferably, the sensor membranes 40 are cast polyvinyl chloride film structures which are loaded with an ionophore selective to a particular constituent or ion in the fluid sample being analyzed. Thus, for example, the ionophore for any particular one of the sensors 32 may be chosen so as to allow selective determination of a particular analyte species in a blood sample, in accordance with conventional practices well known to those skilled in the art. As such, the sensor arrays 24, 26 may provide multiple signals regarding numerous individual analyte species for a particular fluid sample. The sensor wells 38 are filled with a conventional ion transport hydrogel electrolyte 42. As is well known, the hydrogel electrolyte 42 serves to contain water and ions so that the electrical potential established from one face to the other of the membranes 40 can be measured by internal sensing electrode 34a and an external electrochemical reference electrode (not shown) in contact with the fluid in the flow channel 15. Preferably, during storage and/or shipment, a suitable conditioning fluid occupies the internal volume of the flow cell to maintain operational conditioning of the sensors.

Figure 9:
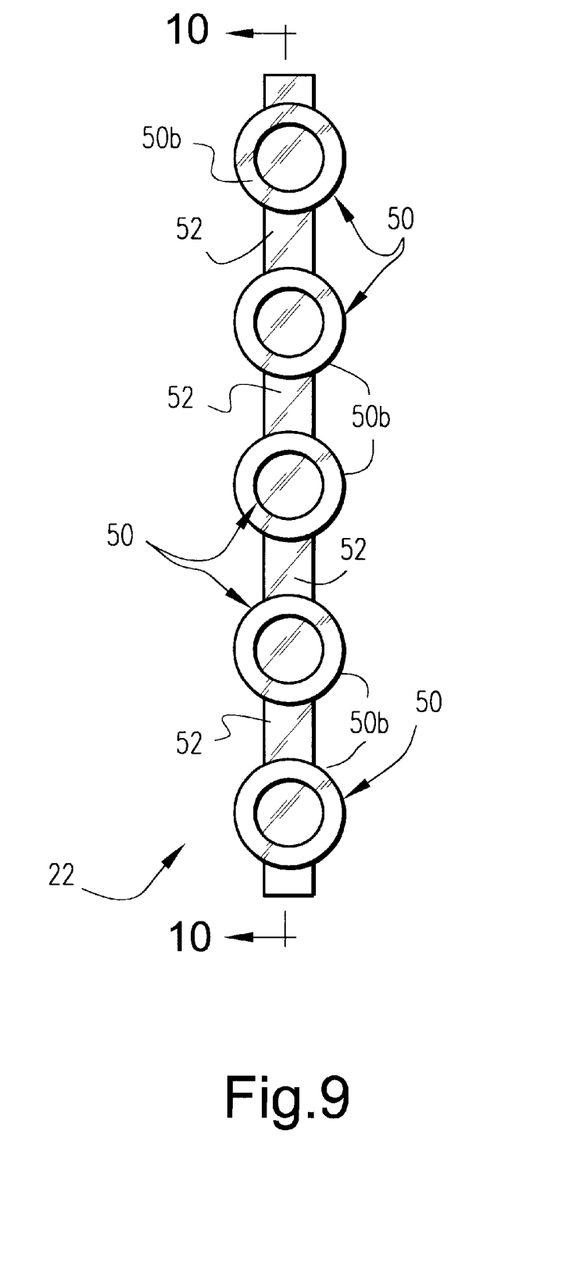
FIG. 9 is a planar view of a representative preferred elastomeric biasing member employed in the sensor cartridge depicted in FIG. 1.
Figure 10:
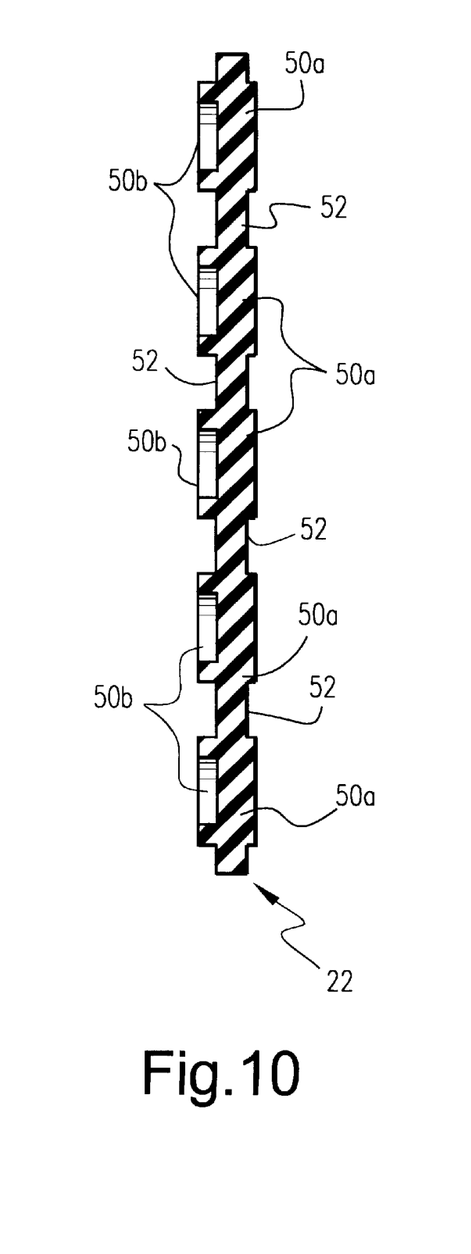
FIG. 10 is a cross-sectional view of the biasing member depicted in FIG. 7 as taken along line 8—8 therein.

As briefly discussed above, the membranes 40 are in direct sealing contact with a respective one of the lands 24a, 26a surrounding the sensor ports 24, 26. This sealing contact is encouraged by the biasing members 20, 22 as will be explained in greater detail with reference to accompanying FIGS. 9 and 10. In this regard, FIGS. 9 and 10 depict in greater detail the biasing member 22. Biasing member 22 is, however, representative of biasing member 20 except that the latter is provided with one less biasing pad corresponding in number to the sensor ports 26 and sensors 32 provided on the sample cell face 14b and the sensor array 16, respectively. Thus, the discussion which follows with respect to biasing member 22 is equally applicable structurally and functionally to the biasing member 20 and, wherever possible, structures of biasing member 20 which are visible in the accompanying drawing FIGURES corresponding to structures of biasing member 22 are noted below parenthetically..

As can be seen in FIGS. 9 and 10, the biasing member 22 (20) is a one-piece structure formed from any suitable resilient, shape-retaining elastomeric material (e.g., silicone rubber). Specifically, the biasing member 22 (20) includes a series of generally cylindrically shaped biasing pads 50 (51) interconnected to one another in series by bridge regions 52

(53). Each of the biasing pads 50 (51) includes a solid base 50a (51a) and a cup-shaped face formed by annular wall 50b (51b).

In use, the biasing members 20, 22 will be seated within a correspondingly configured recess 54 (see FIGS. 2 and 3) in the housing components 12a, 12b such that the cup-shaped faces formed by annular walls 50b, 51b project toward the back surface of the support substrates 30, 31 of the sensor arrays 16, 18. The terminal edges of the annular walls 50b, 51b will thus cause a compressive force to be exerted against the sensor arrays 16, 18 thereby urging the sensor membranes thereof into direct sealing contact with their respective land surfaces 24a, 26a. That is, since the annular walls 50b, 51b are sized sufficiently to substantially coaxially circumscribe the sensor ports 24, 26 exposed on the lands 24a, 26a, the bias force exerted thereby will manifest itself in a uniform fluid-tight seal being established between the peripheral region of the membranes 40 bounding the sensor wells 38 of the individual sensors 32 and a respective one of the lands 24a, 26a. With the housing components 12a, 12b coupled to one another therefore, the sensor cartridge 10 is capable of detecting multiple physical parameters and/or constituents in a fluid sample flowing through the sample cell 14.

The sensors 32, 33 have been depicted as being formed into an array whereby the sensors are disposed along a common, continuous ceramic substrate. Thus, as depicted in the accompanying drawing FIGS. 1–2 and 7–8, for example, the sensors 32, 33 are structurally connected to one another by means of the common substrate 30, 31. However, individually removable (and hence interchangeable) sensors could also be provided. In such a situation, a bank of separate, discrete sensors could be disposed on individual chips, structurally unconnected to one another except by the common, surrounding housing. Such an embodiment of this invention is depicted in accompanying FIG. 11. In either case, a "sensor array" as that term is employed herein is meant to refer to multiple individual sensors which are disposed along a common continuous substrate structure (e.g., as depicted in accompanying FIGS. 1–2 and 7–8), or a bank of separate discrete sensors disposed on individual chips and structurally unconnected to one another except by the common surrounding housing (e.g., as depicted in accompanying FIG. 11).

Figure 11:
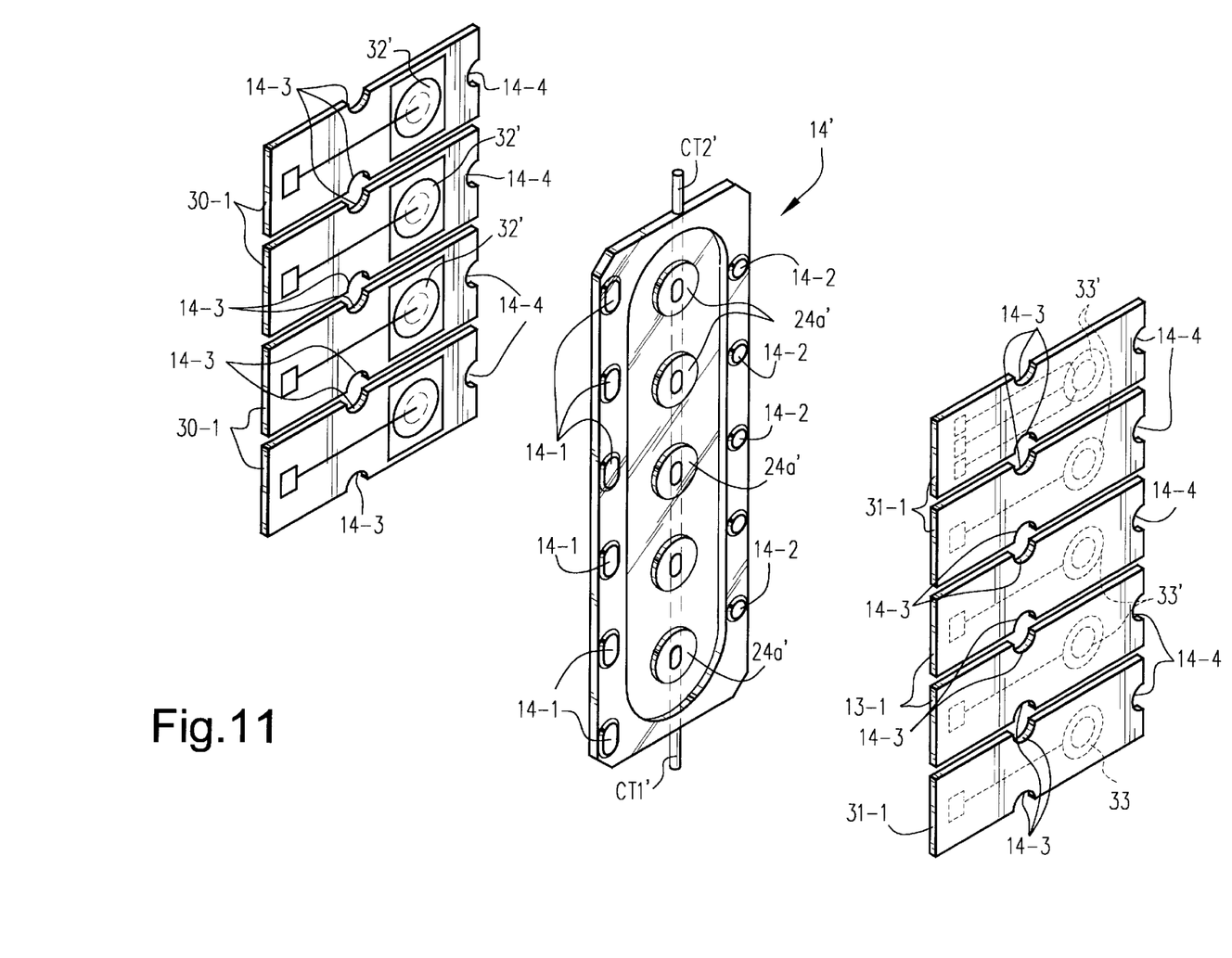
FIG. 11 is an enlarged perspective view of another particularly preferred embodiment of the sample cell and sensor arrays employ key structures to ensure proper orientation of the individual sensor structures of the sensor arrays in the cartridge of the present invention.

Specifically, in FIG. 11, structures which correspond to those already discussed have been identified by the same reference numeral but additionally are identified by a prime (') designator. Hence, such corresponding structures which have already been described will not be further discussed here.

The principal difference between the structures depicted in FIG. 11 and those already described above is that each of the individual sensors 32', 33' is provided on a separate, discrete substrate 30-1, 31-1, respectively. In such a manner, individual ones of the sensors 32', 33' which determine respective specific individual constituents of a bodily fluid may be "packaged" with one another within the housing 12 so as to provide a cartridge assembly 10 that satisfies a user's individual needs and/or requirements. Moreover, providing the sensors 32', 33' on individual substrates 30-1, 31-1, allows one or more of the substrates 30-1, 31-1 to be easily removed and/or replaced so as to provide different detection capabilities to the cartridge 10 and/or discard single failed sensors before final assembly during manufacturing (i.e., without having to discard good sensors).

It is particularly preferred that the sample cell 14' and the individual sensor substrates 30-1, 31-1 be provided with cooperating key structures which serve to properly align and orient the sensors 32', 33' and their respective electrical connection pads relative to the one another and to the housing 12. Particularly, the sample cell 14' is provided along its edges with a series of raised arcuate lateral and forward key bosses 14-1, 14-2, respectively. Adjacent pairs of lateral key bosses 14-1 thus mate with correspondingly configured arcuate key recesses 14-3 of each of the substrates 30-1, 31-1 when positioned against the surface of the sample cell 14'. In addition, each of the forward key bosses 14-2 mates with a respective one of the forward arcuate key recesses 14-4 provided in the substrates 30-1, 31-1. It will, of course, be understood that, although only one face of the sample cell 14' can be seen in the accompanying FIG. 11, its opposite face is likewise provided with a mirror image arrangement of bosses 14-1, 14-2, respectively. In such a manner, therefore, the substrates 30-1, 31-1 will be accurately and reliably positioned and oriented in the cartridge 10.

As can now be appreciated, the sensor cartridge 10 according to this invention achieves several advantages over known prior art sensors. For example, since the sensor membranes are in direct sealing contact with the sample cell, the sensor membrane area and volume are no longer dictated by flow channel dimensions. Moreover, the self-sealing sensor arrays according to the present invention when positioned in the housing structures are self-aligning with their respective sensor ports.

It should be understood that the number of sensor ports and sensors shown in the accompanying drawing FIGURES is exemplary only. Thus, more or less than the number of sensor ports and sensors depicted herein could be provided without departing from the scope of this invention.

Furthermore, the discussion above has focused on ion-selective electrodes as one embodiment of the sensors 32, 33. However, virtually any sensor may be employed in the successful practice of this invention. For example, when detecting gas and non-ionic analytes (e.g., sensors to detect oxygen, lactate and glucose constituents in a blood sample), amperometric sensors may be employed in addition (or as an alternative) to ion-selective sensors in the arrays 16, 18. As one exemplary embodiment, the four sensors 32 in the sensor array 16 may be amperometric sensors while the five sensors 33 of the sensor array 18 may be ion-selective sensors. Therefore, as used herein, the term "sensor" is used generically to cover electrochemical sensing of virtually any desired analyte, as well as chemiluminescent and other optical sensors.

As is now apparent from the discussion above, the present invention offers numerous advantages over known prior art sensor cartridges, such as, for example:

(1) The required sample volume is defined by the dimensions of the flow channels and not by the size of the individual sensors in the array.

(2) Since the dimensions of the flow channel can be reduced to limits defined only by the fluid properties of the samples, the flow channel can be designed with smaller cross-sectional area. Longer flow channel length and greater separate between sensors are possible than with conventional linear flow-through channel designs in which the sensor array(s) compose one or more walls of the flow channel.

(3) Since the membrane cross-section no longer defines the flow channel width, the total membrane volume can be advantageously increased by increasing the membrane cross-section, that is, without increasing the membranes' thickness and impedance.

(4) The increase in total membrane volume increases the available reservoir of critical membrane material, extending use-life and shelf-life.

(5) The larger membrane cross-section provides a larger surface area for bonding membranes to the substrate and for sealing membranes to the flow channel.

(6) The membrane itself provides its own sealing gasket (i.e., is self-gasketing).

(7) The membrane is mechanically captured between two layers, the substrate supporting the membrane and the layer defining the flow channel.

(8) The large membrane cross-section compared to the membrane area exposed to the sample advantageously reduces precision requirements for membrane deposition.

(9) Significantly longer path lengths against impedance degradation are provided between sensors and between other electrical components, conductors, tracks and the like.

(10) The longer path lengths, together with the increased bonding and sealing surface area between components will allow wet storage and, therefore, short preconditioning time after the sensor cartridge is installed.

(11) The zig-zag flow path allows the use of single, discrete sensor chips in one or more measurement channels without introducing additional sealing problems.

Other, further, advantages ensue from the use of single, discrete sensors, which has been made specifically and conveniently possible by the structural and functional features of this invention, notably, the clamshell housing and zig-zag flow channel. For example, in certain cases, important advantages may be gained by separating the individual sensor components of a multi-sensor array into shorter sensor clusters or even single, discrete sensors. In the prior art, realizing these advantages involved introducing and solving a large number of additional leakage/sealing problems associated with each junction between the separate sensor chips and significantly increased the mechanical complexity of the sensor cartridge. The zig-zag flow path design of the present invention, however, allows the use of single, discrete sensor chips for one or more channels in the sensor array; it does so without introducing any new or additional sealing problems at the junctions between adjoining sensor chips. In contrast to the flow path in conventional linear flow designs, the sample does not flow across the full width of each sensor membrane and then across the junctions between neighboring sensors, but jumps along a zigzag path contacting each sensor at or near its center only. Thus, sensor chips can be simply disposed side-by-side, one for each species measured, to form the sensor array for the sensor module without concern that the junctions between the individual chips will provide a multiplicity of additional leak paths.

Important manufacturing advantages result from the module design based on single, discrete sensor chips, which in turn, is made possible by the zig-zag flow channel design. As a result, individual sensors can be manufactured in conveniently large clusters of identical sensors of the same composition, of the same design, and intended to measure the same species. These sensors may then be separated on the ceramic plate by suitable perforations in the substrate material, to allow them to be easily snapped apart into conveniently smaller clusters for preliminary tests. The sensors can be separated further into individual sensor chips and reassembled appropriately, each for a different species, into arrays according to the requirements of the sensor module.

Thus, in contrast to the sensor cartridges of the prior art, it will not be necessary to manufacture sensor arrays in the same configuration and sequence as will be required in the final product. The present invention thus allows sensors to be manufactured in arrays of identical sensors, tested, and later snapped apart, and then reassembled into composite clusters containing multiple sensors each for a different species as required for the final product. As a result, the manufacturing controls necessary to dispense very small amounts of volatile and critically formulated membrane "cocktail" solutions of very different compositions into a tightly packed network of shallow receptacles are enormously reduced.

Further, the present invention importantly reduces the cost, complexity and size of the hardware and software associated with membrane deposition. More generally, for all sensors manufactured, there is a much reduced chance of cross-contamination during membrane deposition if all sensors deposited on any one manufacturing plate are identical.

Manufacturing arrays of identical sensors, moreover, eases the additional constraints placed on the design of miniature sensors which are to be manufactured in compact arrays. In order to exploit the economies of bulk manufacture in compact arrays, it is necessary that all sensors in each manufacturing run have the same general design and structure involving more or less identical manufacturing procedures. This, of course, would be true without compromise for arrays of identical sensors.

The possibility of abutting single, discrete sensors (or small clusters) without introducing any new or additional sealing problems provides another advantage related to the problem of overall manufacturing yield. Thus, poor overall yields would inevitably result for an integrated cluster of several sensor units, each of which has a manufacturing yield non-trivially less than 100%. To improve yields, therefore, larger sensor clusters of identical sensors may be manufactured, pre-tested and then broken up into single sensors. The "failed" sensors may thus be easily discarded with the acceptable sensors being reassembled into composite arrays.

The single sensor chip approach may be especially appropriate for one channel or more to address specific circumstances and problems, for example: a sensor channel with structure very different from others; a sensor channel with low manufacturing yield; and a single channel with hybrid structure.

Therefore, some exemplary advantages that ensue from the use of single, discrete sensor chips in accordance with the present invention include:

(1) Each sensor can be tested before being included in the sensor cartridge.

(2) Failed sensors can be discarded individually before the cost of assembling them into the sensor cartridge is incurred.

(3) Failed sensors can be discarded individually without the sacrifice of good sensors that would otherwise be clustered together with them.

(4) All sensors during any manufacturing run will have in all details substantially the same design, composition and fabrication technique.

(5) The possibility of contaminating the composition of one type sensor with trace components of another during manufacture is reduced to inconsequence.

(6) Manufacturing and test equipment, software and procedures will be greatly simplified since they need to accommodate only one design at a time.

(7) Any sensor which requires a very different design, structure or fabrication techniques (e.g., the oxygen sensor) can be more simply and readily manufactured in a totally separate manufacturing run.

Although several advantages that ensue from the present invention have been enumerated above, it may be apparent to those skilled in this art that other advantages may result. Thus, while the present invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A sensor cartridge for determining desired fluid sample constituents comprising:
    a housing;
    a rigid flow-through sample cell having a fluid sample inlet and outlet positioned within said housing;
    a flow channel defined entirely internally of said sample cell between said inlet and outlet;
    multiple sensor ports defined in at least one external face of said sample cell which are in fluid communication with said flow channel; and
    a sensor array comprised of multiple planar sensors each being operatively associated with a respective sensor port, wherein
    each of said sensors includes (i) a support substrate having front and rear surfaces, (ii) an electrochemical sensor supported by said support substrate on said front surface thereof, and (iii) a membrane covering both said electrochemical sensor on said front surface of said support substrate and said respective sensor port so as to be in contact with a portion of the fluid sample to determine a desired constituent of the fluid sample; and wherein
    each said membrane includes a peripheral region entirely surrounding said respective sensor port in direct sealing contact with said external face of said sample cell, and wherein
    said sensor cartridge further comprises a biasing member positioned between said housing and a rear surface of said support substrate such that said peripheral regions of said membranes are compressively captured between said front surface of said support substrates of said sensors and said external face of said sample cell to provide a self-sealing gasket therebetween; and wherein
    said flow channel is fluid-isolated from said sensors except for fluid-contact with the sensor membranes covering said respective sensor ports.

2. A sensor cartridge as in claim 1, wherein multiple ones of said sensor ports are defined in one and another of opposite faces of said flow-through sample cell, and wherein said flow channel alternately fluid-connects in series sensor ports defined in said one of said sample cell faces and sensor ports defined in said another of said sample faces.

3. A sensor cartridge as in claim 2, wherein said flow channel defines a zig-zag flow path.

4. A sensor cartridge as in claim 1, wherein said sample cell has a recessed face which establishes a land surface, and wherein said sensor ports are positioned at said land surface.

5. A sensor cartridge as in claim 1, wherein said housing is a two-part, bilaterally symmetrical housing.

6. A sensor cartridge as in claim 1, wherein said biasing member includes a generally cylindrical biasing pad formed of a resilient elastomeric material.

7. A sensor cartridge as in claim 6, wherein said biasing pad includes a base for contacting said housing, and an annular face wall for contacting said sensor.

8. A sensor cartridge as in claim 6, wherein said housing includes a channel recess to receive said biasing pad.

9. A sensor cartridge as in claim 1, comprising a conditioning fluid filling said flow channel and said sensor ports for maintaining operational conditioning of said sensors.

10. A sensor cartridge as in claim 1, comprising multiple individual support substrates, each said support substrate supporting a respective one of said multiple sensors.

11. A sensor cartridge as in claim 10, wherein said support substrates and said sample cell include cooperating key structures which ensure correct placement and orientation of said sensors relative to said sample cell.

12. A sensor cartridge as in claim 11, wherein said key structures include raised bosses formed on said sample cell and recesses formed on said substrates which cooperate with said bosses.

13. A sensor cartridge as in claim 1, comprising a common support substrate for supporting at least one array of said multiple sensors.

14. A fluid sensor cartridge comprising:
    a housing;
    a sample cell having at least one recessed face defining a series of land surfaces positioned within said housing;
    a flow channel defined within said sample cell;
    a series of sensor ports in fluid-communication with said flow channel and exposed at respective ones of said land surfaces;
    a planar sensor support substrate having front and rear surfaces; and
    a sensor array supported on said front surface of said sensor support substrate and positioned adjacent to said sample cell, said sensor array having a series of multiple planar sensors each in registry with a respective one of said sensor ports, wherein
    each of said multiple planar sensors includes (i) an electrochemical sensor, and (ii) a membrane covering both said electrochemical sensor and said respective sensor port so as to be in contact with a portion of the fluid sample to determine a desired constituent of the fluid sample; and wherein said membranes include peripheral regions entirely surrounding said respective sensor port in direct sealing contact with said external face of said sample cell, and wherein
    said fluid sensor cartridge further comprises a biasing member positioned between said housing and said rear surface of said support substrate which compressively sandwiches said peripheral regions of said membranes between said front surface of said sensor support substrate and said external face of said sample cell to provide a self-sealing gasket therebetween.

15. A sensor cartridge as in claim 14, wherein each said electrochemical sensor of said sensor array includes an electrochemical electrode, an electrical conductive layer, a water-impermeable layer disposed over a portion of said electrical conductive layer and defining a sensor well in registry with a terminal end of said electrode, wherein said membrane of each said multiple planar sensor of said sensor array cover a respective said sensor well.

16. A sensor cartridge as in claim 15, wherein said water-impermeable layer is a ceramic glaze layer.

17. A sensor cartridge as in claim 14, wherein said biasing member is a one-piece structure formed of a resilient elastomeric material.

18. A sensor cartridge as in claim 17, wherein said biasing member includes a plurality of generally cylindrical biasing pads in substantial coaxial alignment with a respective one of said sensor ports.

19. A sensor cartridge as in claim 18, wherein said biasing pads include an annular face wall in contact with said sensor array.

20. A fluid sensor cartridge comprising:

a sample cell defining a flow channel and at least two exposed sensor ports in fluid-communication with said sample cell;

at least two planar sensors each having (i) a support substrate having opposed front and rear surfaces, (ii) an electrochemical sensor supported by said support substrate on said front surface thereof so as to be in covering relationship with a respective one of said sensor ports, and (iii) a membrane covering said electrochemical sensor;

a housing for said sample cell and said sensors; and an elastomeric biasing member positioned between said housing and said rear surface of said support substrate for urging said membranes covering said electrochemical sensors on said front surface of said support substrate into sealing contact with said sample cell.

21. A sensor cartridge as in claim 20, wherein said biasing member includes a generally cylindrically shaped biasing pad formed of a resilient elastomeric material.

22. A sensor cartridge as in claim 21, wherein said biasing pad includes an annular face wall in contact with said rear surface of said support substrate.

23. A sensor cartridge as in claim 22, wherein said biasing member is formed of silicone rubber.

24. A sensor cartridge as in claim 20, wherein said sample cell includes a recessed region which defines a land surface, and wherein said sensor port is exposed onto said land surface.

25. A sensor cartridge as in claim 24, wherein said membrane includes a peripheral region which is in direct sealing contact with said land surface surrounding said sensor port.

26. A sensor cartridge as in claim 20 or 25, wherein said electrochemical sensor includes an electrochemical electrode, a water-impermeable layer disposed over said electrode and defining a sensor well in registry with a terminal end of said electrode, wherein said membrane of said sensor covers said sensor well.

27. The sensor cartridge of claim 26, wherein said water-impermeable layer is a ceramic glaze layer.

28. A fluid sensor cartridge comprising:

a flow-through sample cell defining a flow channel and having opposed separated planar faces;

a series of separated sensor ports defined in said opposed separated planar faces and fluid-connected to said flow channel;

said planar faces of said sample cell having recessed regions which establish land surfaces surrounding respective ones of said sensor ports;

first and second sensor arrays sandwiching said sample cell, said first and second sensor arrays having individual planar sensors in registry with a respective one of said sensor ports; wherein said individual planar sensors include (i) a planar support substrate having opposed front and rear planar surfaces, (ii) an electrochemical sensor disposed on said front surface of said support substrate so as to be in opposition with said respective one of said sensor ports, and (iii) a membrane covering said electrochemical sensor and having a peripheral region which surrounds said respective one of said sensor ports;

a housing containing said first and second sensor arrays and said sample cell sandwiched therebetween, and biasing members positioned between said housing and each said rear surface of said planar support substrate so as to bias said membranes into sealing contact with said land surfaces of said respective ones of said sensor ports.

29. A sensor cartridge as in claim 28, wherein said biasing members include individual biasing pads in registry with a respective one of said individual sensors of said sensor arrays, and formed of an elastomeric material for urging said membranes of said individual sensors of said first and second sensor arrays into contact with respective ones of said land surfaces.

30. A sensor cartridge as in claim 29, wherein said individual biasing pads include an annular face wall in contact with said rear surface of said planar support substrate of said sensor array and positioned in substantial coaxial alignment with respective ones of said sensor port.

31. A sensor cartridge for the simultaneous determination of respective fluid sample constituents comprising:

a flow-through sample cell having a fluid inlet, a fluid outlet and a zig-zag flow channel defined between said fluid inlet and outlet;

a series of sensor ports defined in external faces on each of the opposed sides of said flow channel which are in fluid communication with said flow channel;

first and second sensor arrays each located on a respective external face of said sample cell and having at least one planar sensor which is self-aligning with respect to a respective one of said sensor ports;

each said sensor including a membrane component having a central region in covering relationship with said respective one of said sensor ports so as to be in contact with the fluid sample in the flow channel, whereby a respective fluid sample constituent may be determined, and a peripheral region which surrounds said central region and said respective one of said sensor ports so as to be in contact with a respective external face of said sample cell; and a two-part housing which comprises a biasing member positioned between said housing and a rear surface of a sensor support substrate, wherein the housing compressively seals said peripheral region of said membranes directly to said respective external face of said sample cell and thereby be self-gasketing against leakage of the sample fluid.

32. The sensor cartridge of claim 31, wherein said housing includes openings along one surface to allow electrical and/or fluid connections between said sensors and a host analyzer.

33. The sensoe cartridge of claim 31, wherein said sensors include a supporting substrate, and a water-impermeable layer disposed over said substrate to define sensor wells.

34. The sensor cartridge of claim 33, wherein said water-impermeable layer is a ceramic glaze.

35. The sensor cartridge of claim 33 or 34, wherein said peripheral region of said membrane component is in direct bonding contact said water-impermeable layer.

36. The sensor cartridge of claim 31, wherein said membrane component includes an ionophore component which is selective to a particular constituent of the sample fluid, and wherein said peripheral region has a volume in excess of the volume of the central region so as to provide a reservoir of the ionophore component sufficient to replenish the ionophore component depleted from said central region.

37. The sensor cartridge of claim 31, wherein each said sensor is individually removable.

38. The sensor cartridge of claim 31, wherein said sensors are disposed along, and are structurally interconnected by, a common substrate structure.

* * * * *